(12) United States Patent
Scoggins

(10) Patent No.: US 6,378,698 B1
(45) Date of Patent: Apr. 30, 2002

(54) INFANT'S DISPOSABLE FLUORIDE TOOTH WIPES

(76) Inventor: Katrina M. Scoggins, 8037 Roanoke St., Philadelphia, PA (US) 19118

( * ) Notice: Subject to any disclaimer, the term of this patent is extended or adjusted under 35 U.S.C. 154(b) by 0 days.

(21) Appl. No.: 09/671,672

(22) Filed: Sep. 28, 2000

Related U.S. Application Data

(60) Provisional application No. 60/173,293, filed on Dec. 28, 1999.

(51) Int. Cl.[7] .............................................. B65D 81/24
(52) U.S. Cl. ...................... 206/205; 206/63.5; 206/494; 15/227
(58) Field of Search ................................ 206/205, 210, 206/233, 63.5, 494, 368, 361, 362, 409, 812; 15/167.1, 227; 132/309; 433/89, 216

(56) References Cited

U.S. PATENT DOCUMENTS

| D46,510 S | 10/1914 | Over |
| 1,530,459 A | 3/1925 | Carmichael |
| 2,966,691 A | 1/1961 | Cameron |
| 3,138,820 A | 6/1964 | Sterling |
| 3,452,382 A | 7/1969 | Kazdan |
| 3,749,296 A | * 7/1973 | Harrison ..................... 206/205 |
| 3,754,332 A | 8/1973 | Warren, Jr. |
| 3,784,055 A | * 1/1974 | Anderson .................... 206/494 |
| 3,902,509 A | 9/1975 | Tundermann et al. |
| 4,171,047 A | * 10/1979 | Doyle et al. ................. 206/210 |
| 4,180,160 A | * 12/1979 | Ogawa et al. ............... 206/210 |
| 4,219,129 A | * 8/1980 | Sedgwick .................... 206/210 |
| 4,335,731 A | 6/1982 | Bora, Jr. |
| 4,831,676 A | 5/1989 | Denmark |
| 4,972,946 A | * 11/1990 | Whittaker .................... 206/210 |
| 5,076,424 A | * 12/1991 | Nakamura ................... 206/205 |
| 5,487,201 A | 1/1996 | Hansen et al. |
| 5,771,522 A | 6/1998 | Carmody |

FOREIGN PATENT DOCUMENTS

| GB | 780443 | 7/1957 |
| GB | 1164121 | 9/1969 |

* cited by examiner

Primary Examiner—Luan K. Bui
(74) Attorney, Agent, or Firm—Richard C. Litton

(57) ABSTRACT

A disposable dental wipe made of a material substrate of predetermined size and dimensions for use in wiping the teeth, gums, and oral mucosa of an infant is provided. The dental wipes are impregnated with fluoride to strengthen erupted and growing teeth. Use of the dental wipes depends upon sensory pressure nerve endings in the user's fingers to quantitate the pressure at the time of cleaning. Fluoride may be impregnated onto the wipe for introduction into the oral cavity through any suitable composition, including gels, pastes, and powders, but is preferably introduced through an aqueous solution. Also included is a dental wipe dispenser for storing the wipes for ready usage.

18 Claims, 5 Drawing Sheets

INFANT'S DISPOSABLE FLUORIDE TOOTH WIPES

CROSS-REFERENCE TO RELATED APPLICATION

This application claims the benefit of U.S. Provisional Patent Application Serial No. 60/173,293, filed Dec. 28, 1999.

BACKGROUND OF THE INVENTION

1. Field of The Invention

The present invention relates to devices for oral hygiene. More particularly, the device relates to disposable fluoride-impregnated dental wipes for infants and children.

2. Description of Related Art

Numerous devices have been devised for providing enhanced dental care for persons of all ages. Some of the most significant advances have involved the use of improved teeth cleaning instruments for daily use. Other techniques have centered around the development of fluoridated compositions for application to the teeth to prevent caries and to strengthen the teeth. However, none of the conventional solutions or techniques described hereinbelow provide an easy and effective device or method for fulfilling the daily oral health care and hygiene needs of infants and small children, especially regarding the need of children of these ages for fluoride to strengthen teeth and prevent cavities, which is often unmet under existing circumstances. For example, U.S. Pat. No. 1,530,459, issued to Carmichael, discloses a dentifrice package and carrier comprising a dentifrice container having its walls composed of a fabric which is impregnated with polishing material. A separate quantity of polishing material is removably contained within the container. The container is adapted to be opened to expose its contents to allow it to be used as a napkin to polish the teeth and to massage the gums.

U.S. Pat. No. 2,966,691, discloses a finger tip tooth cleaner comprising upper and lower layers of sheet material connected together so as to provide a pocket open at one end for receiving the finger tip of a user. Stretched elastic means are fixed to the layers, which are stiff enough when dry to hold the elastic means against contraction and are flexible enough when wet to permit contraction and thereby shrink the pocket.

U.S. Pat. No. 3,138,820, issued to August, discloses a disposable tooth cleaning and gum massaging device adapted for insertion into the mouth consisting essentially of a thin, semi-rigid, tightly compressed cellular sponge member, composed of a large number of interconnecting pores. The pores contain a dentifrice which is released when the device is chewed, softening it and causing it to expand from the moisture in the mouth.

U.S. Pat. No. 3,452,382, issued to Kazdan, shows a tooth cleaning device comprising a finger-compressible fibrous body, pliable when wetted and adapted for insertion into a human mouth. The fibrous body is impregnated and coated with a dentifrice polishing and abrasive tooth cleaning composition containing pumice and a water-soluble saccharide binding agent.

U.S. Pat. No. 3,754,332, issued to Warren, Jr. describes a device for use in the treatment of caries in the teeth. The device has fluoride or other chemicals which are carried by a section of the device which may be detachable. The device is worked between two teeth at a contact area to place the detachable section in contact with the teeth. The chemical agent is applied to the detachable section either before or after it is placed in contact with the teeth. The detachable section remains between the teeth when the rest of the member is removed, and preferably dissolves in the mouth when wet.

U.S. Pat. No. 3,902,509, issued to Tundermann et al., shows a disposable device for cleaning teeth in which the device is made of a high wet strength material which is shaped and sealed in the form of a "pocket" or flat thimble. Adhering to the outer surface of the device are various flavored substances and dental powders or pastes, such as polishing or bacteriostatic agents. The thimble is slipped over a finger and rubbed over all the surfaces of the teeth to remove the adhering food and plaque films which cause stains and mouth odors.

U.S. Pat. No. 4,335,731, issued to Bora, Jr., discloses a disposable device for cleaning teeth composed of a flexible, soft honeycombed sheet. Bristles composed of integral fibers extend outward from the exposed surface of the sheet. The sheet is secured over the finger which is used for massage of the user's gums and cleaning of the user's teeth. In the preferred form, the sheet is impregnated with a dentifrice.

U.S. Pat. No. 4,831,676, issued to Denmark, discusses a dental prophylaxis device comprising a pair of absorbent core members, saturated with dental cleansing material and enclosed in a spaced-apart disposition within a suturable covering layer having a roughened surface. The device is insertable in the mouth to clean and massage teeth and gums.

U.S. Pat. No. 5,487,201, issued to Hansen et al., shows a oral wipe comprising a sleeve composed of interwoven material, a pick element, and a piece of dental floss. The pick element comprises a heat sealable component in which the piece of floss is embedded.

U.S. Pat. No. 5,771,522, issued to Carmody, discloses a dental hygiene wipe for cleaning exterior surfaces and interproximal areas of teeth. The device includes a flexible base substrate having an abrasive cleaning pad coupled to the base substrate. The abrasive cleaning pad includes a plurality of quarter-spherical projections which can be used to effect cleaning and polishing of tooth enamel. The abrasive cleaning pad is preferably comprised of a porous material which can be impregnated with a dentifrice, mouth wash, or other moist substances. Foreign Patents granted to Bachmaier (BR 780,443) and Rose (BR 1,164,121) disclose improvements in cleaning devices. And lastly, U.S. Design Pat. No. 46,510, issued to Over, illustrates a sanitary tooth cleaner.

None of the above inventions and patents, taken either singly or in combination, is seen to describe the instant invention as claimed.

SUMMARY OF THE INVENTION

The disposable dental wipes according to the invention comprise a material substrate of predetermined size and dimensions for use in wiping the teeth, gums, and oral mucosa of an infant and for introducing fluoride into the oral cavity to strengthen erupted and growing teeth and to prevent caries. Use of the dental wipes depends upon sensory pressure nerve endings present in the user's fingers to quantitate the pressure at the time of cleaning. The wipe is specially sized to comfortably fit in the user's hand to clean the mouth of a small child. Fluoride may be impregnated onto the wipe through any suitable composition, including gels, pastes, and powders, but is preferably introduced through an aqueous solution. Also included in the invention is a dental wipe dispenser comprising a housing having a hinged lid with an air-tight seal. The pre-moistened wipes comprise a continuous sheet having an elongated or longitudinal direction. The sheet is folded into separate connected wipes which are demarcated from each other by a line of perforations extending from one free lateral edge of the sheet to the opposite free lateral edge. In an alternative embodiment of the invention, the dental wipe may have at least one finger stall on either side for the reception of a thumb or finger.

Accordingly, it is a principal object of the invention to provide a disposable dental wipe which is dimensioned and sized for insertion into a child's mouth, which will release fluoride into the oral cavity for the prevention of caries, and which may be applied to the surfaces of the mouth by manipulation of the fingers.

It is another object of the invention to provide a tooth and mouth cleansing device for children and infants which does not require additional external sources of water.

It is a further object of the invention to provide a disposable dental wipe which may be conveniently carried in a dispenser.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS.

Figure 2:
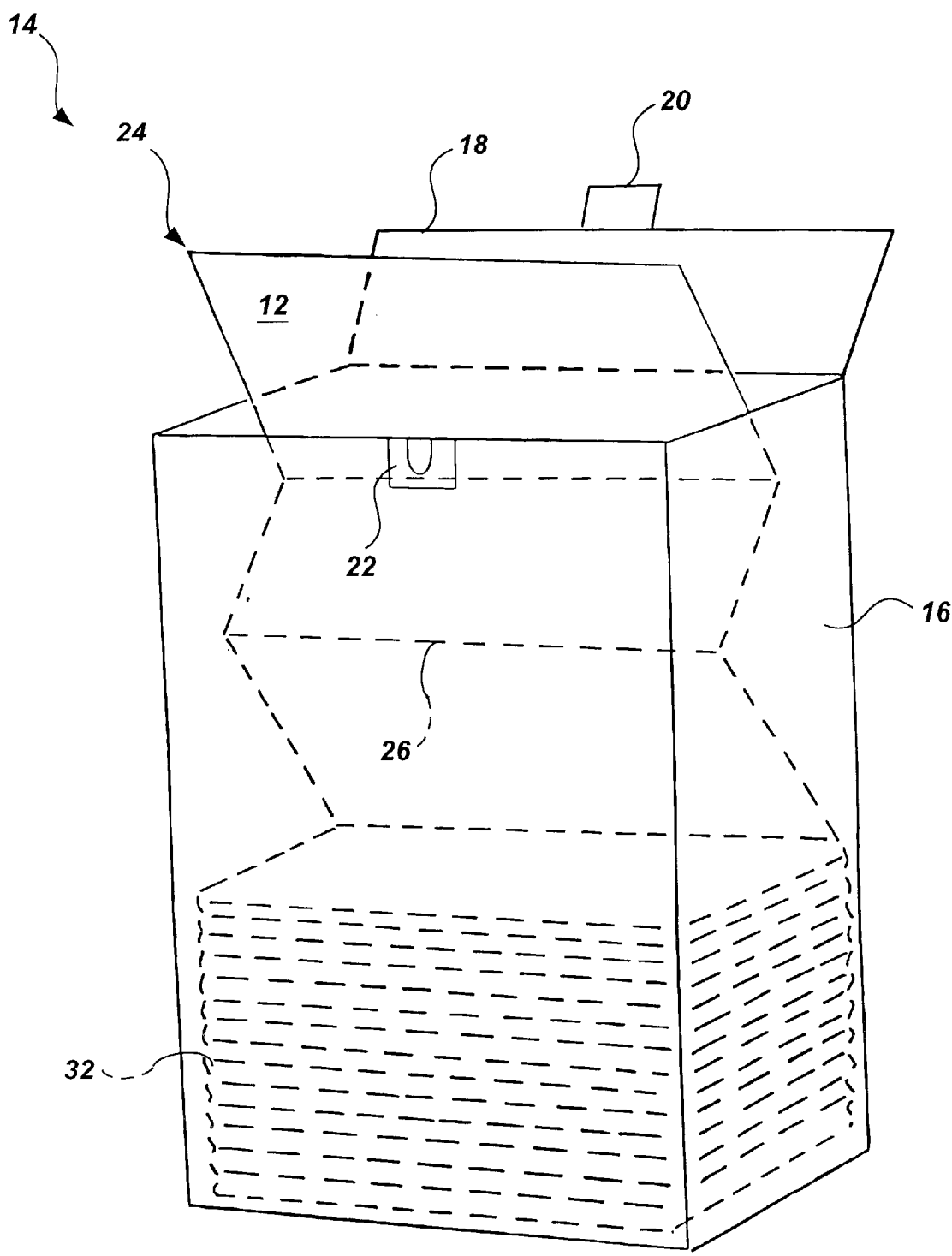
FIG. 2 is front view of the dispenser, according to the invention, illustrating a stack of wipes inside of the dispenser as indicated by phantom lines.
Figure 3:
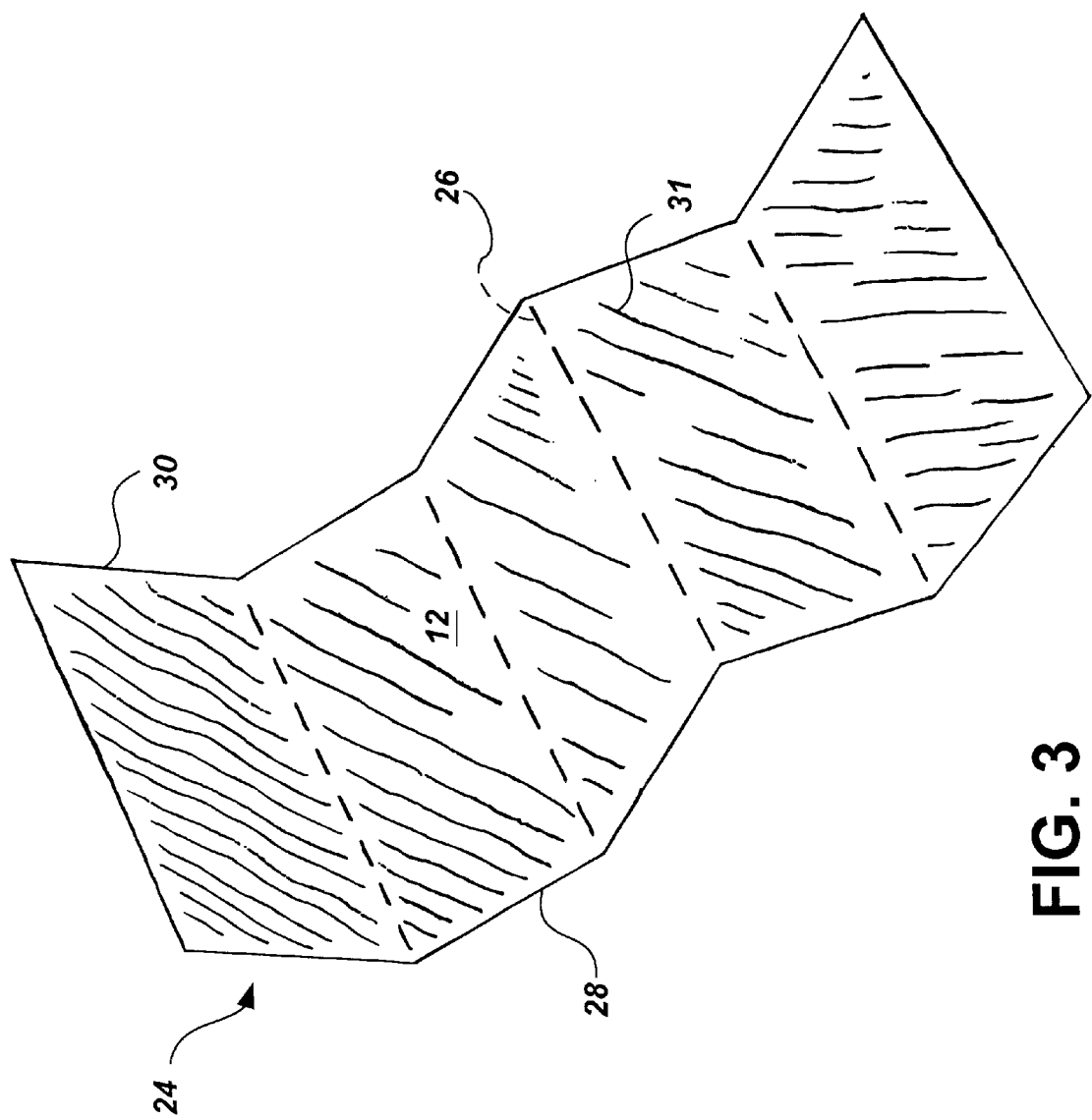
FIG. 3 is a side angle view of a portion of a roll of wipes, according to the invention.

The present invention provides disposable dental wipes for infants and children. The preferred embodiment of the invention is depicted in FIGS. 1–3, and is generally referenced by numeral 10.

Figure 1:
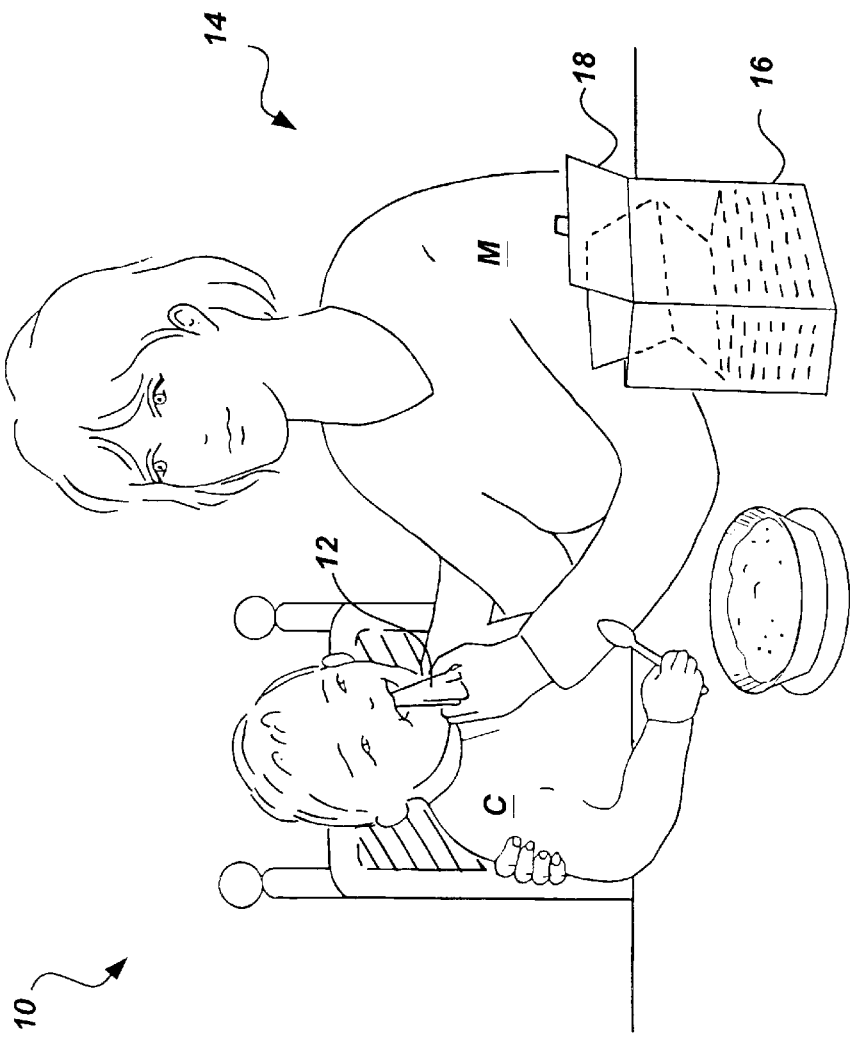
FIG. 1 is an environmental, perspective view of infant's disposable fluoride tooth wipes according to the present invention, illustrating a woman manually cleansing a young child's mouth using the dental wipe.

As diagrammatically illustrated in FIG. 1, a user M is shown wiping the teeth, gums, and oral mucosa of her child C using the pre-moistened, fluoride impregnated dental wipe, generally 12, of the present invention. The user M relies upon the sensory pressure nerve endings in her fingers to quantitate the correct pressure to apply to the teeth during cleaning. Use of tactile sensation alone is sufficient to prevent enamel erosion and cementum abrasion, which are frequent problems of toothbrush cleaning. The user M and child C enjoy numerous benefits through the use of the wipe 12, including increased sanitation since wipes 12 are designed for one-time use and are disposed thereafter.

As can be observed from the illustration, the wipe 12 is specially sized to comfortably fit in the user's hand to clean the mouth of the small child C. In the preferred embodiment of the invention, the wipe 12 is substantially 2.5 inches in length and width, but this specification embraces alternative embodiments of all dimensional sizes. However, the optimal range of sizes for both length and width is between 2 and 3 inches.

While the wipe 12 is preferably made of polymeric material, it may be formed of any suitable material, including cloth, polyurethane, high wet strength paper, polyethylene, or any essentially waterproof material which is suitably strong, durable, and not liable to fray during use. It is especially important that the wipe 12 be made of a material that does not come apart so as to prevent the introduction of foreign material into the respiratory or gastrointestinal systems of infants.

Modern medicine and dentistry have long observed the positive correlation between children's oral hygiene and their general health and well being. However, because children's teeth are impermanent, some parent's fail to grasp the extreme importance of good oral and dental hygiene at an early age. The American Academy of Pediatric Dentistry (AAPD) recommends that preventive dentistry begin at an early age. Children with successful regimens of oral health care chew their food better, enjoy improved nutrition, learn to speak at an earlier age, and generally have healthier lives.

The AAPD recommends that children between 6 months and 16 years of age receive appropriate quantities of fluoride to prevent tooth decay. Fluoride systematically strengthens tooth enamel both internally, before the teeth erupt, and externally after their development. Thus, appropriate amounts of fluoride can have an enormous impact on the health of a child. Many parents resort to bottled waters during the early years of their children's lives believing that it will be healthier for them; unfortunately though, bottled waters typically do not contain biologically sufficient levels of fluoride as recommended by the AAPD. It is axiomatic that small children can not adequately brush their teeth and thereby benefit from fluoride toothpaste. Additionally, busy parents may not always have the time to brush their childrens' mouths after every meal, snack, or intake of sweets. And so this invention addresses an important need.

The pre-moistened dental wipes 12 of this invention comprise an absorbent substrate carrying a preferably aqueous fluoride liquid composition impregnated into the substrate. However, the fluoride may be impregnated onto the wipe through any suitable composition, including gels, pastes, and powders having various encapsulated or other flavors. The wipes are useful to remove trace particles of food or other intraoral extraneous matter, as well as the normal residue which accumulates on the teeth secondary to eating. The present invention allows the user to coat the teeth and oral mucosa of their children with a thin layer of aqueous solution containing fluoride in a safe and controlled manner. Important mineral sources of fluoride which are commonly known in the art include sodium fluoride, stannous fluoride, potassium fluoride, and ammonium fluoride.

The liquid loading level of the wipes 12 should not exceed the absorbance capacity of the substrate from which the wipe 12 is made in order to function not only as a solution distribution means with some absorptive capacity, but also to distribute the aqueous fluoride solution without introducing excessive amounts into the mouth. In children aged 2 to 4, excessive amounts of fluoride can lead to enamel fluorosis or discoloration of the teeth. Therefore, low levels of aqueous fluoride may be employed to allow for frequent usage of the wipes 12.

Additional substances may be included in the aqueous solution, including standard dentifrices, as well as germicidal and flavor producing agents. It may also be desirable to include one or more bacteriostatic and fungistatic agents to act as a preservatives. The aqueous solution may also contain minor but effective amounts of a fragrance selected so as to be aesthetically and chemically compatible.

Also depicted in FIGS. 1–3, is a dental wipe dispenser 14 which includes a body or housing 16 having a hinged lid 18. The lid 18 preferably conforms as closely as possible to the outer configuration of the housing 16 so as to provide an air-tight seal. In the side angle view depicted in FIGS. 1–2, the housing 16 can be seen to have a generally rectangular cross-section. However, in alternative embodiments of the invention, the dispenser 14 may be circular, square, or have any suitable and appropriately shaped housing 16 so as to allow for easy dispensing of the dental wipes 12. The dispenser 16 may be made of any suitable material, though it is preferably made of polymeric material.

In the preferred embodiment of the invention, the lid 18 is hinged to a rear portion of the housing, for example, with a plastic hinge, integral with the lid 18 and housing 16. A pin hinge is also acceptable. At the front end of the lid 16 there is preferably a lid latch 20 with a mating catch 22 on the front of the housing 16, which serves for sealing the contents of the housing 16 to render it substantially air-tight to prevent the wipes 12 from drying out prior to use.

In alternative embodiments of the invention, the housing 16 may also comprise a slotted opening for dispensing wipes 12 therethrough. The slotted opening can contain a serrated edge for permitting one or more dental wipes 12 to be severed from the continuous sheet of wipes and to prevent the stack of wipes 12 from being removed from the container. The slotted opening can be closed using any device such as commonly known and used in the art to prevent evaporation of the pre-moistened wipes, including a hinged flap.

As shown in FIG. 3, the pre-moistened wipes 12 may be defined as a continuous, elongated sheet 24 having an elongated or longitudinal direction. The sheet 24 is folded into separate connected wipes 12 which are demarcated from each other by a line of perforations 26 extending from one free lateral edge 28 of the sheet 24 to the opposite free lateral edge 30, and has fluoride, generally 31, impregnated thereon. As most clearly shown in FIG. 2., the sheet 24 is folded in a substantially zig zag overlay pattern which defines a single uniform generally rectangular-shaped packet or stack 32 of wipes 12 with each wipe 12 being separated one from the other by the spaced tear perforations 26. The folded zig zag configuration may result in the perforations being positioned at the midpoint between the front and back of each stack 32 of wipes 12. Alternatively, the tear perforations 26 may be positioned at the fold line. Various other positions and patterns of folding and separation are possible and are embraced by this specification.

Figure 4A:
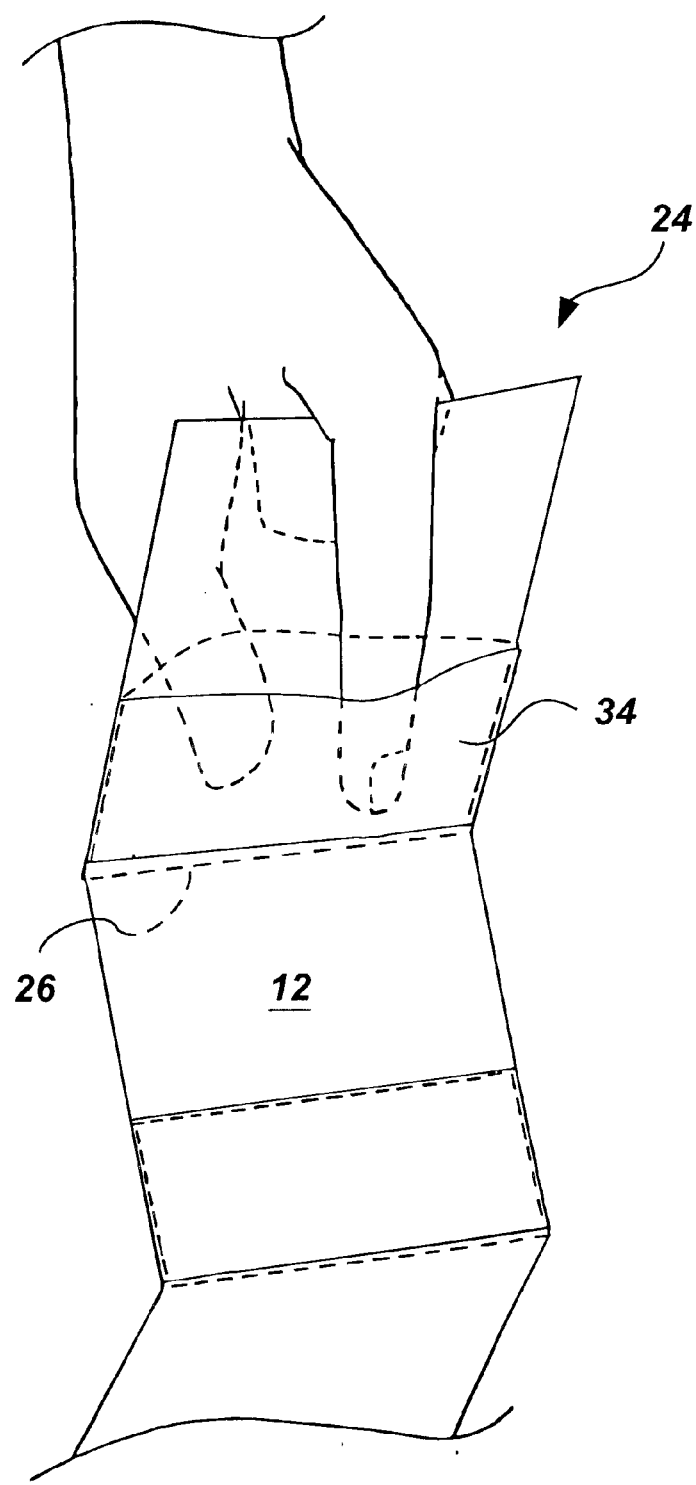
FIG. 4A is a front view of a wipe, according to a second embodiment of the invention.
Figure 4B:
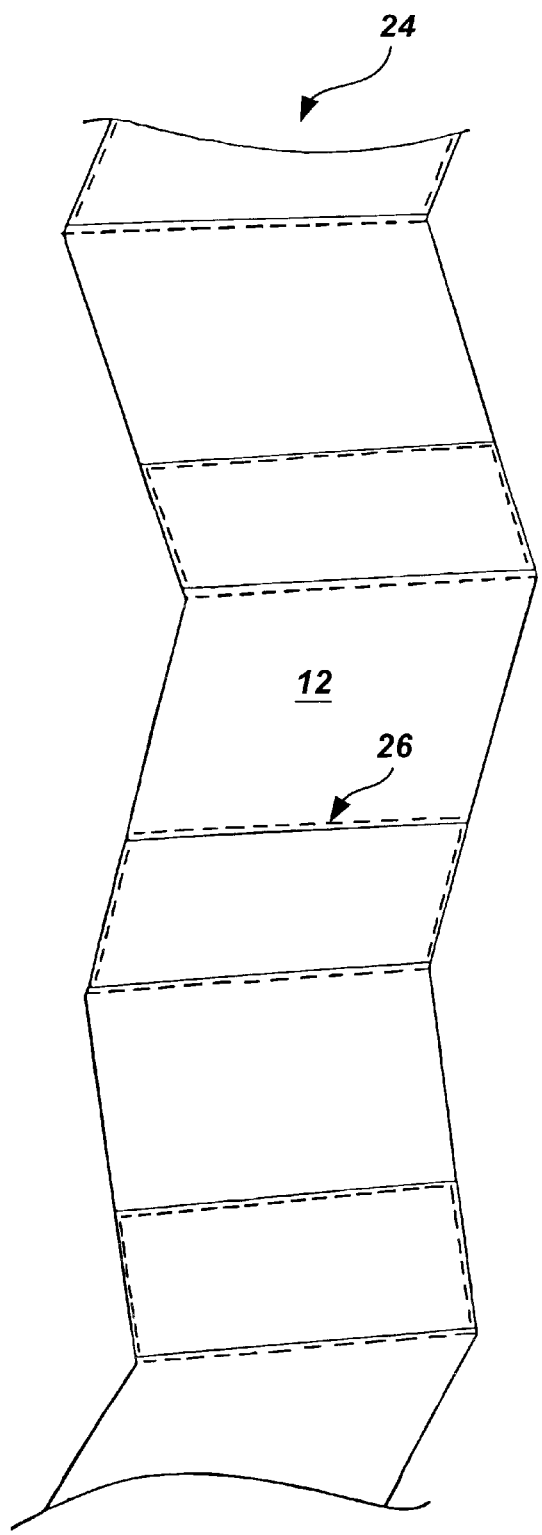
FIG. 4B is a front view of a wipe, according to a second embodiment of the invention.

As shown in FIG. 4A, in an alternative embodiment of the invention, the dental wipe 12 may have at least one finger stall, generally 34, on either side for the reception of a thumb or finger. The finger stalls 34 may be formed by folding a first sheet in half, inserting a second sheet into the valley portion of the first sheet, and attaching the first and second sheets together in such a manner as to create a wipe 12 having sleeve-like portions, shaped and dimensioned to receive a finger, substantially as shown in FIG. 4A. Alternatively, this specification embraces all other means for providing finger stalls 34 or portions such as commonly known in the art or in conventional usage. As in the preferred embodiment of the invention, this second embodiment may be formed into a continuous, elongated sheet for separation therefrom when needed by the user, as shown in FIG. 4B.

It is to be understood that the present invention is not limited to the sole embodiments described above, but encompasses any and all embodiments within the scope of the following claims.

I claim:

1. In combination, dental wipes for children and an associated dispenser for the dental wipes comprising:

(a) a continuous sheet of wipes having a pair of generally parallel, spaced-apart free lateral edges, said sheet comprising a plurality of individual said wipes having connected sections defined by spaced, tear-apart perforations extending from said free lateral edge to opposite said free lateral edge, each of said tear-apart perforations comprising a series of spaced-apart slits through said wipes, said wipes being dimensioned for use in the oral cavities of children for cleaning their teeth, gums, and oral mucosa;

(b) a wipe dispensing container, having a top hingedly connected to said container, said top sufficiently sealable to said container to prevent escape of moisture, said container being dimensioned to receive a plurality of said wipes; and (c) fluoride impregnating said sheet.

2. The dental wipe of claim 1, wherein said fluoride is any fluoride containing compound.

3. The dental wipe of claim 1, wherein the amount of said fluoride is sufficient to increase formation of fluorapatite formation of teeth enamel.

4. The dental wipe of claim 1, wherein said fluoride is in an dental-caries-inhibiting amount.

5. The dental wipe of claim 1, wherein said fluoride is aqueous fluoride.

6. The dental wipe of claim 1, wherein said fluoride is selected from the group consisting of sodium fluoride, stannous fluoride, potassium fluoride, ammonium fluoride and combinations thereof.

7. In combination, dental wipes for children and an associated dispenser for the dental wipes comprising:

(a) a continuous sheet of wipes having a pair of generally parallel, spaced-apart free lateral edges, said sheet comprising a plurality of individual said wipes having connected sections defined by spaced, tear-apart perforations extending from said free lateral edge to opposite said free lateral edge, each of said tear-apart perforations comprising a series of spaced-apart slits through said wipes, said wipes having at least one finger stall attached to said wipes, said at least one stall being dimensioned to receive at least one finger, said at least one finger stall being for allowing a user to manipulate said wipe in the oral cavity of a child to allow for more thorough cleaning of the oral cavity, said wipes being dimensioned for use in the oral cavities of children for cleaning their teeth, gums, and oral mucosa;

(b) a wipe dispensing container having a top hingedly connected to said container, said top sufficiently sealable to said container to prevent escape of moisture, said container being dimensioned to receive a plurality of wipes; and (c) and fluoride impregnating said sheet.

8. The dental wipe of claim 7, wherein said fluoride is any fluoride containing compound.

9. The dental wipe of claim 7, wherein the amount of said fluoride is sufficient to increase formation of fluorapatite formation of teeth enamel.

10. The dental wipe of claim 7, wherein said fluoride is in an dental-caries-inhibiting amount.

11. The dental wipe of claim 7, wherein said fluoride is aqueous fluoride.

12. The dental wipe of claim 7, wherein said fluoride is selected from the group consisting of sodium fluoride, stannous fluoride, potassium fluoride, ammonium fluoride and combinations thereof.

13. The dental wipe of claim 7, wherein said fluoride is aqueous fluoride.

14. The dental wipe of claim 13, wherein said fluoride is selected from the group comprising sodium fluoride, stannous fluoride, potassium fluoride, ammonium fluoride and combinations thereof.

15. The dental wipe of claim 14, wherein the amount of said fluoride is sufficient to increase formation of fluorapatite formation of teeth enamel.

16. The dental wipe of claim 14, wherein said fluoride is in an dental-caries-inhibiting amount.

17. The dental wipe of claim 14, wherein said fluoride is aqueous fluoride.

18. The dental wipe of claim 14, wherein said fluoride is selected from the group consisting of sodium fluoride, stannous fluoride, potassium fluoride, ammonium fluoride and combinations thereof.

* * * * *